United States Patent
Liu et al.

(10) Patent No.: US 12,110,561 B2
(45) Date of Patent: Oct. 8, 2024

(54) NON-INVASIVE DETECTION METHOD FOR SCREENING FOR A WELL-DEVELOPED BLASTOCYST

(71) Applicant: Guangzhou nvwa Life Technology Co., Ltd., Guangdong (CN)

(72) Inventors: Jiang Liu, Beijing (CN); Jie Qiao, Beijing (CN); Guoqiang Li, Beijing (CN); Yang Yu, Beijing (CN); Yong Fan, Guangdong (CN); Congru Li, Beijing (CN)

(73) Assignee: Guangzhou NVWA Life Technology Co., Ltd., Guangdong (CN)

( * ) Notice: Subject to any disclaimer, the term of this patent is extended or adjusted under 35 U.S.C. 154(b) by 269 days.

(21) Appl. No.: 16/093,545

(22) PCT Filed: Apr. 11, 2017

(86) PCT No.: PCT/CN2017/080102
§ 371 (c)(1),
(2) Date: Oct. 12, 2018

(87) PCT Pub. No.: WO2017/177900
PCT Pub. Date: Oct. 19, 2017

(65) Prior Publication Data
US 2019/0161811 A1    May 30, 2019

(30) Foreign Application Priority Data
Apr. 12, 2016 (CN) .................... 201610225668.5

(51) Int. Cl.
| | | |
|---|---|---|
| C12Q 1/68 | (2018.01) | |
| C07H 21/04 | (2006.01) | |
| C12Q 1/6881 | (2018.01) | |
| C12Q 1/6888 | (2018.01) | |

(52) U.S. Cl.
CPC ............. *C12Q 1/6888* (2013.01); *C12Q 1/68* (2013.01); *C12Q 1/6881* (2013.01); *C12Q 2600/154* (2013.01)

(58) Field of Classification Search
None
See application file for complete search history.

(56) References Cited

U.S. PATENT DOCUMENTS

| | | |
|---|---|---|
| 9,458,506 B2 | 10/2016 | Chavez |
| 2012/0016184 A1* | 1/2012 | Yao .................. G16H 50/50 600/33 |
| 2015/0119282 A1 | 4/2015 | Chavez |
| 2016/0108475 A1* | 4/2016 | Porreca ............. C12Q 1/6883 506/2 |
| 2020/0080150 A1* | 3/2020 | Shamonki ........... C12Q 1/6883 |

FOREIGN PATENT DOCUMENTS

CN       102985926 A       3/2013

OTHER PUBLICATIONS

Wright et al. (Fertility & Sterility, vol. 92, No. 3, Supplement S25-26, Oct. 19, 2009) (Year: 2009).*
White et al. (Scientific Reports, vol. 5, vol. 17311, pp. 1-16, Dec. 2, 2015) (Year: 2015).*
Urman et al. (Curr Opin Obstet Gynecol, vol. 19, pp. 273-278, 2007) (Year: 2007).*
Mccallie et al. (PLoS, vol. 11, No. 7, e0159507, pp. 1-14, Jul. 19, 2016) (Year: 2016).*
Li et al. (J. of Genetics and Genomics, vol. 44, pp. 475-481, 2017) (Year: 2017).*
Liao et al (BMC Genomics, vol. 16 (Suppl 12): 511, Sep. 2015). (Year: 2015).*
Farlik et al. (Cell Reports, vol. 10, pp. 1386-1397, 2015).*
Gardner, D.K. et al., "Blastocyst score affects implantation and pregnancy outcome; towards a single blastocyst transfer", Fertil Sterril, vol. 73, No. 6, Jun. 30, 2000 pp. 1155-1158.
Hao, Yan et al., "Imprinting methylation and assisted reproductive", Journal of Reproduction & CONTRACEPTION, vol. 26, No. 2, Jun. 30, 2015 pp. 112-120.
International Search Report, mailed Jul. 18, 2017 in connection with PCT International Application No. PCT/CN2017/080102.

* cited by examiner

*Primary Examiner* — Jeanine A Goldberg
(74) *Attorney, Agent, or Firm* — Fish & Richardson P.C.

(57) ABSTRACT

A DNA methylation profile of a few of trophectoderm cells in a blastocyst is detected, and the average methylation 5 level and the methylation pattern of embryos identified as having a good morphology in Gardner morphological blastocyst grading process are used as the standard for screening for well-developed blastocysts. The nearer the methylation level of the trophectoderm cells of the blastocyst to be tested approaches the methylation level or state of the good embryo, the better the embryo development is and the higher the 10 suitability for being implanted into a maternal subject is.

1 Claim, 4 Drawing Sheets

NON-INVASIVE DETECTION METHOD FOR SCREENING FOR A WELL-DEVELOPED BLASTOCYST

CROSS-REFERENCE TO RELATED APPLICATIONS

This application is a § 371 national stage of PCT International Application No. PCT/CN2017/080102, filed Apr. 11, 2017, claiming priority of Chinese Patent Application No. 201610225668.5, filed Apr. 12, 2016, the contents of each of which are hereby incorporated by reference into the application.

TECHNICAL FIELD

The invention relates to the field of epigenetic informatics at a genome-wide level, specifically, to a non-invasive detection method for screening for a well-developed blastocyst.

BACKGROUND ART

In vitro fertilization and embryo transplantation (IVF-ET), known as "test-tube baby", is a special clinical assisted reproductive technology. IVF is the process of fertilization by taking eggs and sperm samples, and then manually finishing fertilization under an in vitro controlled environment. In this process, early embryo is then transplanted to the uterus, and develops into a fetus. The babies born using such in vitro fertilization are also called 'test-tube babies'. The in vitro fertilized embryos need to be screened before implantation. There are two clinical screening methods at present:

(1) Gardner morphological blastocyst grading system. During IVF-ET, the culture and transplantation of a blastocyst is one important step. The quality of blastocysts is one of the most important factors which influence the success of IVF-ET. At present, Gardner morphological blastocyst grading system is applied clinically. According to the blastocoel's size and the hatching status, the blastocyst development is divided into 6 stages. Stage 1: a cavity is existed in the blastocyst at an early stage, with a blastocoel cavity smaller than half the volume of the embryo. Stage 2: blastocoel cavity is equal to or larger than half the volume of the embryo. Stage 3: full blastocyst, with the blastocoel cavity completely filling the volume of embryo. Stage 4: expanded blastocyst, with the blastocoel cavity completely filling the volume of embryo, the total volume of the embryo become larger, and the zona pellucida become thinner. Stage 5: hatching out of the blastocyst, and part of the blastocyst is escaped from the zona pellucida. Stage 6: hatched blastocyst, and all of the blastocyst is escaped from the zona pellucida. The blastocysts at stage 3 to 6 also require quality grading of their inner cell mass ICM and trophectoderm cells (CTE cells). IM grades: grade A, many cells and cells are tightly packed: grade B, few cells, and cells are loosely grouped; grade C, very few cells. TE grades: grade A, many cells form epithelium with a compact structure; grade B, a few cells form a loose epithelium; grade C, epithelium is formed by sparse cells. According to the grading method, the best blastocyst should be 3AA grade blastocyst on the fifth day, as well as the 4AA grade blastocyst on the sixth and seventh day. During the assisted reproductive technology (ART) treatments, AA grade blastocysts are ideal for embryo transplantation. However, in clinical practice, only 33% of couples can obtain AA grade embryos for implantation, and 52% of patients can only obtain B* grade blastocysts (including AB, BA and BB). The birth rate for AA grade blastocysts is 39%, and for B* grade blastocysts is approximately 28%. However, the birth rate for C* grade blastocysts (including BC and CB) is 4%, and wherein the birth rate for CC grade blastocysts is almost zero.

Gardner morphological blastocyst grading system is traditional embryo morphology which selects embryos with a high morphological level for transplantation, and it relies on traditional microscopical techniques and has a low accuracy. Data from clinical trials showed that, for assisted reproductive therapy only using morphological detection, the abortion rate of patients with recurrent abortion is 33.5% and the clinical pregnancy rate is 45.8%. Since the average success rate of 'test-tube baby' is about 20% to 30%, 2 to 3 blastocysts will be implanted into a uterus at the same time in order to increase the success rate of implantation. As a result, multifetal pregnancy often happens. Multifetal pregnancy is riskier than single pregnancy, and this risk exists for both mother and babies. Hence, for the safety of mother and babies, fetal reduction needs to be carried out in principle when the number of fetus exceeds three. However, fetal reduction may cause all the embryos aborted at a chance of 10%.

As a result, new methods are needed to improve the success rate of 'test-tube baby' and to avoid the hazards and ethical conflicts brought by fetal reduction during pregnancy that is caused by multi-fetal pregnancy resulting from the transplantation of multiple embryos that are carried out for the purpose of increasing the success rate of pregnancy.

(2) Pre-implantation genetic screening/diagnosis (PGS/PGD, also called 'the third generation of test-tube baby'). By analyzing blastomeres with polymerase chain reaction (PCR) technology, Handyside in England successfully performed pregnancy and delivery after embryonic gender selection for sex-linked disease carriers in 1990. This was the first PGS worldwide and ushered in a new era of prenatal screening. In the 1990s, pre-implantation screening technology had been developed rapidly. In 1994, Monne utilized fluorescent in situ hybridization (FISH) technology and succeeded in chromosome aneuploidy screening and gender detection before implantation. Since then, various technologies have been developed, such as multiples-PCR, fluorescence-PCR and M-FISH. In 1998, FISH began to be applied in the PGS of chromosome equilibrium translocation. By selecting normal and balanced gametes or embryos, PGS can markedly decrease recurrent spontaneous abortion rates caused by chromosome translocation. At the same year, commercially available five-color probe began to be applied to screening older women's oocytes and embryos for aneuploidy during PGS. This five-color probe can be used to screen five chromosomes simultaneously: 13, 18, 21, X and Y chromosomes. Since the year of 1999, interphase nuclear conversion technology, comparative genomic hybridization (CGI-H) and whole genome amplification (WGA) are applied to PGS, further facilitating the investigation and application of PGS. Ever since 2010, high-throughput sequencing has begun rapid development. From hundreds of thousands of DNA to millions of DNA can be sequenced at one time, making detailed analysis of embryonic genome possible and bringing PGS to a new dimension. The enthusiasm for research on PGS technology has never decreased at home and abroad. At present, PGS is mainly applied in diagnosing the following genetic diseases: a. abnormality in the number of chromosome; b. pre-implantation gender diagnosis; c. gene deletion type genetic disease; d. diagnosis of embryonic monogenic disorders.

At present, approximately 12% of women of childbearing age in the United States need the help of assisted reproductive technology (ART) to give birth to offspring. In the population with natural pregnancy, a lot of pregnant women suffered from abortion caused by abnormal embryonic development. Likewise, After ART surgery, a significant proportion of embryos are aborted due to abnormal development. Genetic instability is one important reason for abortion, such as various gene mutations, abnormalities in chromosome number and structure. To exclude early human embryos with genetic defects, pre-implantation genetic diagnosis (PGD) has been widely used clinically through the removal of a few cells from trophoderm of an embryo by micromanipulation and subsequent genetic analysis of these cells. At present, PGD technology is widely used in clinical application, and known as "the third generation of test-tube baby", which greatly reduces the abortion rate in patients with recurrent abortion receiving assisted reproductive therapy and improves the clinical pregnancy rate.

PGS pre-implantation gene screening just screen for the genetic disorders in which chromosome number or DNA sequence changes. While infertility or abortion does not mainly result from change of DNA sequence, the majority of miscarriage occurs without any known reasons.

Epigenetic information plays critical roles during animal development. All of the cells in one organism share the same set of DNA genome. However, under the regulation of epigenome, cells differentiate into different types and then form different organs. In other words, cells at different developmental stages during the early development of the embryo must follow a specific epigenomics pattern so as to ensure the totipotency of the embryos and to direct the right differentiation of cells. Genome-wide DNA demethylation occurs during the early embryonic development in mammals. Manually preventing the DNA methylation reprogramming by genetic knock-out of DNA methyltransferases (DNMTs) or gene sequence of Tet3, results in an abnormal embryonic development.

SUMMARY OF THE INVENTION

The present invention provides a non-invasive detection method for screening for a well-developed blastocyst based on pre-implantation epigenetic examination (PEGE). The method firstly uses the epigenetic information to identify the status of an embryo. A few TE cells are separated from an in vitro cultured blastocyst. These cells are non-invasive for the whole blastocyst but they can represent the methylation status and ploidy of each chromosome in the whole embryo.

After the embryo develops into morula, the morula continues cell division. At the same time, the secreted liquid from uterine cavity permeates into the cell through zona pellucida and forms blastocoel. Surrounded the blastocoel are a layer of squamous cells. In this layer, cells have a smaller size, and will develop into a part of placenta, called as trophectoderm (TE) cells. The larger cells accumulated in one end of the embryo are called as inner cell mass (ICM). The cells in ICM are undifferentiated embryonic stem cells with totipotency and will develop into various tissues of fetus. Since TE cells will develop into caul and placenta, a few of TE cells are taken for detection during genetic, thereby such diagnosis does not influence the formation of a normal placenta and fetal development.

The present invention constructs a trace-cell whole-genome methylation library with the "one-tube" method, and then performs whole-genome methylation sequencing of a sample. The average DNA methylation level of AA grade embryos is considered as a standard, which is the quantitative standard for pre-implantation non-invasive detection of embryos. The nearer the methylation status of the tested embryo approaches the value of the standard, the better the developmental status is, the bigger the potential of developing into a normal fetus is, and the higher the suitability for transplantation is. Moreover, whether the chromosome ploidy of the embryo genome is abnormal can be determined by analyzing the methylation data. Embryos with abnormal chromosomes will be rejected for ART. Hence, clinicians can select embryos with normal chromosome ploidy and better epigenetic profile for embryo transplantation by the method of the present invention.

Figure 1:
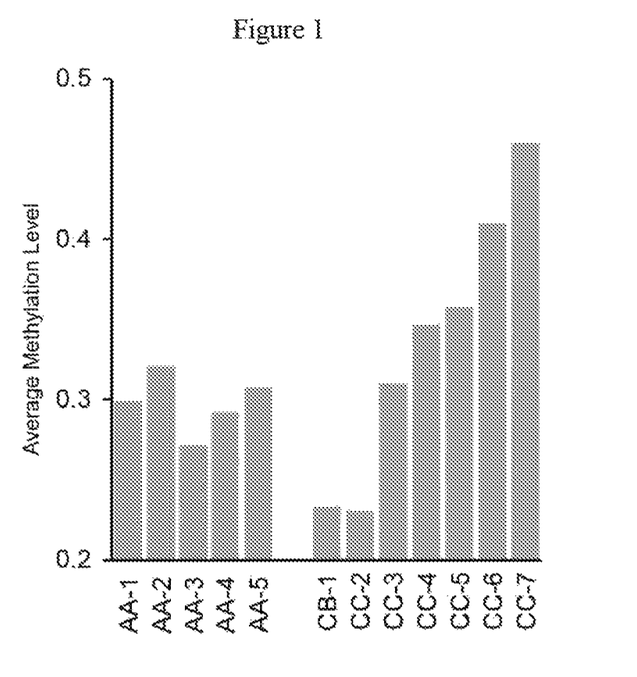
FIG. 1 is a graph showing the DNA methylation level of the AA grade (the highest grade) embryos and CC or CB grade (low grade) embryos. AA-1 and CB-1 embryos were derived from the same parents, and AA-3 and CC-6 embryos were derived from the same parents. The results showed that the DNA methylation level of AA grade embryos were 0.30±0.02, while the DNA methylation level of CC or CB grade embryos, as a whole, were very different from that of AA grade embryos.

The study of the present invention finds that the whole-genome methylation level of embryos identified as AA grade embryos having a good morphology in Gardner morphological blastocyst grading system exhibit a high consistency (FIG. 1); part of embryos identified as B* embryos having a general morphology show a whole-genome methylation level similar to that of the AA grade embryos, and part of the B* embryos have a DNA methylation level dramatically different from that of the AA grade embryos (FIG. 2); and most of C* embryos with a poor morphology show a whole-genome methylation level significantly different from that of the AA grade embryos (FIG. 1). In summary, the worse the grade of embryos in the morphological grading, the greater the proportion of embryos showing a different DNA methylation level as compared with the AA grade embryos.

Figure 3:
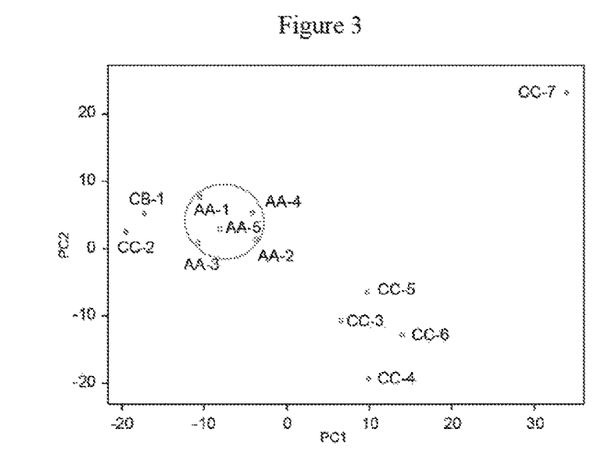
FIG. 3 is a graph showing principal component analysis (PCA analysis) according to the CpG methylation pattern of each embryo. The DNA methylation patterns of AA grade embryos are quite similar, but CC or CB grade embryos show a DNA methylation pattern significantly different from the pattern of AA grade embryos, and the status of each CC or CB grade embryo are significantly different.
Figure 4:
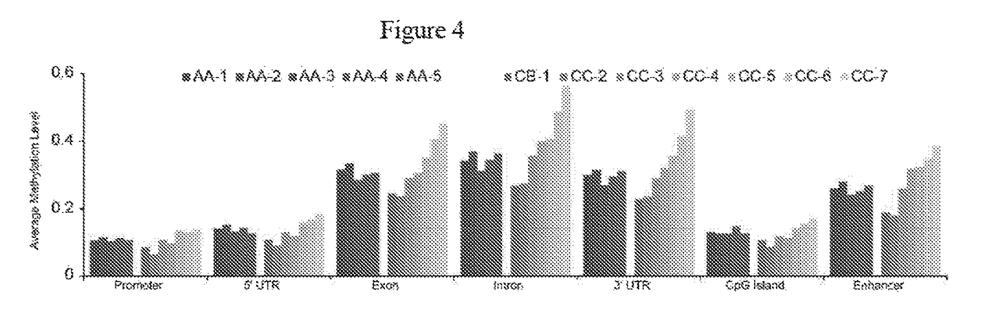
FIG. 4 shows the average DNA methylation levels of different genomic functional elements in 5 AA grade embryos and 7 CB or CC grade embryos. The DNA methylation levels of each functional element of 5 AA embryos are similar, while 7 CC or CB grade embryos show quite divergent DNA methylation levels and most embryos show a DNA methylation level very different from that of AA grade embryos.

Meanwhile, in the present invention, it is also found that the DNA methylation pattern of all AA grade embryos are quite similar (FIGS. 3 and 4), which means that different embryos shows the same high or low methylation status in the same genomic regions. In contrast, embryos with a low quality show quite different methylation status (FIGS. 3 and 4).

Figure 5:
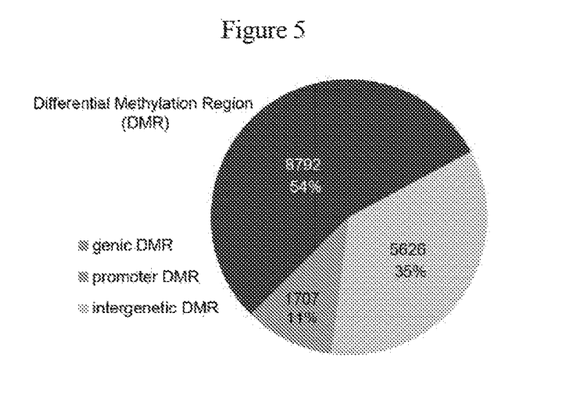
Figure 6:
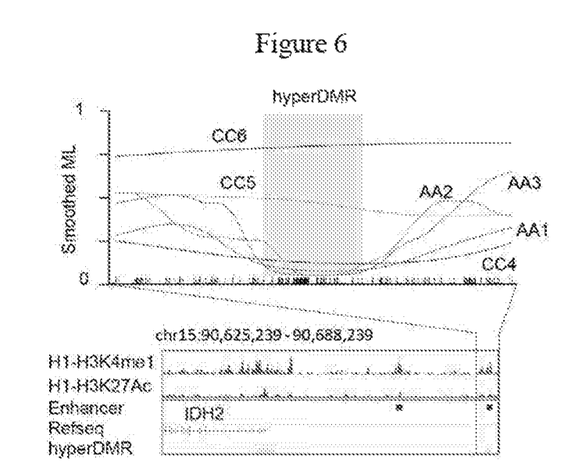
FIG. 6 is a graph showing that the enhancer near IDH2 gene is differentially methylated in different embryos. The figure shows that in high grade and low grade embryos a smoothed DNA methylation level extends within +5 kb of the gene region. The methylation status around enhancer in AA1, AA2 and AA3 are similar, but the methylation status of enhancer in CC5 and CC6 are abnormal. Short black bars indicate CpG sites.
Figure 7:
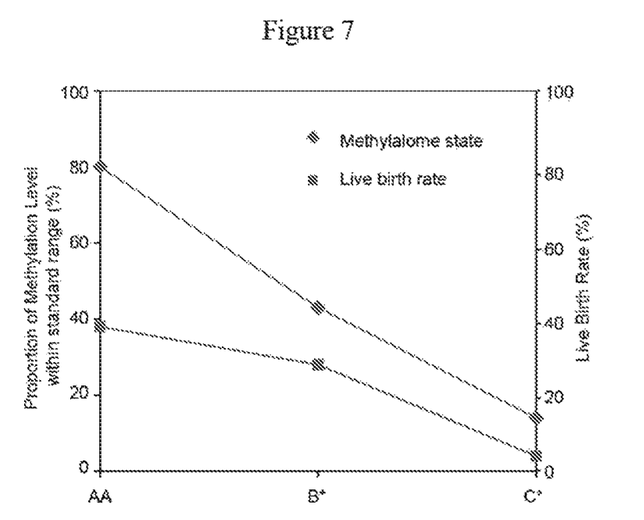
FIG. 7 shows the proportion of embryos with a DNA methylation level falling within 0.30±0.02 in embryos with different grades and the birth rate of embryos with different grades. The birth rate of C* embryos is used to replace the birth rate of CC and C* embryos, so the birth rate of C* embryos is higher than the total birth rate of CC and C* embryos. This figure demonstrates that embryos with better methylation status are prone to have s higher birth rate.

It is proved in the present invention that instability of epigenetic informatics at a whole-genome level frequently occurs during the early embryonic development of human, which could be an important factor which leads to a decreased birth rate in human. The methylation profile of genomic DNA is critical for embryonic development. The regulatory regions for some critical genes are improperly methylated in embryos with abnormal methylation profile (FIGS. 5 and 6). A blastocyst with a DNA methylation level meeting or close to the standard is an ideal candidate for embryo transplantation. Embryos with a DNA methylation level closer to the AA grade embryos may be selected for transplantation by PEGE detection. The epigenetic materials of the embryos can be directly analyzed to determine whether the embryos are abnormally developed, thereby selecting embryos which are more suitable for transplantation. The detection can potentially improve the accuracy of assisted reproductive technology, improve the pregnancy success rate of "test tube baby", reduce the spontaneous abortion rate, improve the quality of pregnancy, and increase the birth rate of "test tube baby" (FIG. 7).

Figure 8:
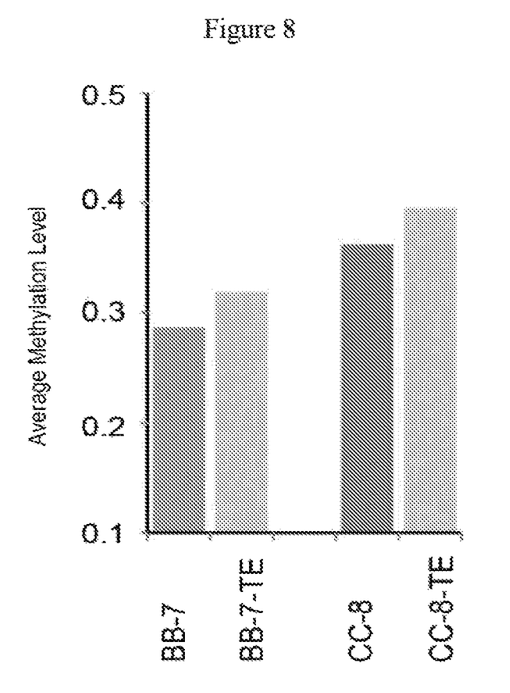
FIG. 8 is a graph showing that the DNA methylation levels of non-invasively biopsied TE cells are similar to that of the whole embryo. BB-7-TE and CC-8-TE are a few of trophectoderm (TE) cells biopsied from BB-7 and CC-8 embryos, respectively.

The DNA methylation level of a few of TE cells biopsied from a blastocyst in a non-invasive manner can represent the whole embryo's DNA methylation level (FIG. 8). Therefore, In the present invention, a few of TE are taken in a non-invasive way firstly, and then the methylation profile of these cells are measured. The average DNA methylation level (0.3±0.02) of the AA grade embryos in the Gardner morphological blastocyst grading system is used as a standard for screening for a well-developed blastocyst. For multiple embryos from the same parents, the blastocyst with a DNA methylation level closer to 0.3 is more suitable for ART.

Previously, an important indicator for detecting whether an embryo can be transplanted is whether the chromosomes of the embryo are abnormal. The measured methylation profile can be used to judge whether the ploidy of each chromosome of an embryo is normal. For example, it was found that many embryos had errors in chromosomes by using the data of methylation profile (Table 2). For example, one extra copy of one large fragment of chromosome 5 and lack of one copy of one large fragment of chromosome 9 were found through analyzing chromosomes of sample s-25-4CC (FIG. 9), indicating that this embryo was not suitable for embryo transplantation.

In summary, the DNA methylation level, DNA methylation pattern and chromosome status can be obtained through measuring the methylation profile of a few of TE cells that are non-invasively biopsied, and thereby clinicians can select embryos with normal chromosome ploidy and better epigenetic profile for embryo transplantation.

Specifically, the present invention provides a non-invasive detection method for screening for a well-developed blastocyst, wherein genome of trophectoderm cells of a blastocyst to be detected is subjected to methylation detection, the average DNA methylation level of embryos identified as having a good morphology in Gardner morphological blastocyst grading system is used as a standard, the blastocyst to be detected is well-developed when its DNA methylation level is close or equal to the standard, and wherein the embryos identified as having a good morphology in the Gardner morphological blastocyst grading system refer to blastocysts of AA, AB, BA and BB grades.

The non-invasive detection method for screening for a well-developed blastocyst according to the present invention further includes using a DNA methylation pattern of embryos identified as having a good morphology in the Gardner morphological blastocyst grading system as the standard.

Furthermore, the non-invasive detection method for screen for a well-developed blastocyst provided by the present invention further includes determining whether the ploidy multiple of each chromosome of the blastocyst is normal according to methylation sequencing results, and the chromosomes of the blastocyst to be tested is normal when the chromosomes are standard diploid chromosomes.

The present invention provides use of the above non-invasive detection method in increasing the rate of pregnancy.

The present invention provides a method for increasing the birth rate of test-tube baby, wherein a blastocyst having a DNA methylation level of trophectoderm cells close or equal to the DNA methylation level of embryos identified as having a good morphology in Gardner morphological blastocyst grading system is selected for embryo transplantation, and the embryos identified as having a good morphology in the Gardner morphological blastocyst grading system refer to blastocysts of AA, AB, BA and BB grades.

A method for increasing the birth rate of test-tube baby further includes selecting a blastocyst to be detected the DNA methylation sequencing results of which show that all chromosomes are standard diploid chromosomes according to DNA methylation sequencing results of trophectoderm cells.

The present invention provides a kit for screening for a well-developed blastocyst, which is a kit for DNA methylation sequencing of a blastocyst, wherein the average DNA methylation level of embryos identified as having a good morphology in Gardner morphological blastocyst grading system is used as a standard, and the blastocyst to be detected is well-developed when its DNA methylation level is close or equal to the standard, and the embryos identified as having a good morphology in the Gardner morphological blastocyst grading system refer to blastocysts of AA, AB, BA and BB grades.

Furthermore, the kit for screening for a well-developed blastocyst of the present invention is a kit for methylation sequencing of a blastocyst, and the blastocyst to be detected is well-developed when DNA methylation sequencing results of the blastocyst show that all chromosomes are standard diploid chromosomes.

Preferably, the detection objects of the kit of the present invention are TE cells of a blastocyst.

The present invention provides use of a DNA methylation level value of embryos identified as having a good morphology in Gardner morphological blastocyst grading system in the preparation of a kit for screening for a well-developed blastocyst, and the embryos identified as having a good morphology in the Gardner morphological blastocyst grading system refer to blastocysts of AA, AB, BA and BB grades.

Specifically, when the genome of the trophectoderm cells of a blastocyst to be tested is subjected to DNA methylation sequencing using the methylation sequencing method as described in the examples of the present invention, and the DNA methylation level of the trophectoderm cells of the blastocyst to be tested falls in the range of 0.3±0.2, the blastocyst is well-developed.

Preferably, the blastocyst to be tested is well-developed when the DNA methylation level of its trophectoderm cells falls in the range of 0.3±0.02.

Further preferably, the blastocyst to be tested is well-developed when the DNA methylation pattern of trophectoderm cells of the blastocyst to be tested is close to the pattern of AA grade blastocysts.

Further preferably, the non-invasive detection method for screening for a well-developed blastocyst further includes determining whether ploidy of each chromosome is normal according to DNA methylation sequencing results, and the chromosomes of the blastocyst to be tested is normal if the chromosomes are standard diploid chromosomes.

Further, the present invention provides a method for increasing the birth rate of test-tube baby, wherein the blastocyst with a DNA methylation level of the trophectoderm cells of 0.3±0.2 is selected for transplantation by using the methylation sequencing method of the present invention.

Preferably, the blastocyst with a DNA methylation level of the trophectoderm cells of 0.3±0.02 is selected for transplantation.

Further preferably, the method of the present invention further includes selecting a blastocyst with standard diploid chromosomes for transplantation according to methylation sequencing results of trophectoderm cells.

The present invention provides a kit for screening for a well-developed blastocyst, wherein the DNA methylation sequencing method as described in examples of the present invention is used, and the blastocyst to be tested is well-developed when the average DNA methylation level of the blastocyst to be tested is 0.3±0.2, and its DNA methylation pattern is similar to that of AA grade blastocysts and/or all chromosomes are standard diploid chromosomes.

Preferably, with respect to the kit of the present invention, the blastocyst to be tested is well-developed when the average DNA methylation level of the blastocyst to be tested is 0.3±0.02, its DNA methylation pattern is similar to that of AA grade blastocysts and/or all chromosomes are standard diploid chromosomes.

Preferably, the detection objects of the kit are trophectoderm cells of a blastocyst.

The present invention also provides use of a DNA methylation level value of embryos identified as having a good morphology in Gardner morphological blastocyst grading system in the preparation of a kit for screening for a well-developed blastocyst. By applying the methylation sequencing method as described in examples of the present invention, the DNA methylation level of AA grade blastocysts is detected to be 0.30±0.02. The nearer the DNA methylation level of a blastocyst to be detected approaches 0.3, the higher the suitability for embryo transplantation.

Meanwhile, the method of the present invention can detect the status of each chromosome in an embryo. Only embryos without abnormal copy numbers in chromosomes can be used for embryo transplantation. In another word, only embryos in which all chromosomes are standard diploid chromosomes can be used for embryo transplantation.

By applying the methylation sequencing method of the present invention, two indicators, i.e., DNA methylation profile (including DNA methylation level) and the status of each chromosome in the embryo, can be obtained at the same time. Embryos are selected for ART by combining these two indicators. The method of the present invention has great advantages over previous methods.

The method of the present invention quantitatively selects a pre-implantation embryo based on the developmental status and the developmental potential of the embryo. The method of the present invention has the same application range as the traditional morphological screening method, and is suitable for all morphologically typed embryos, including AA grade, B* grade or C* grade, but the method of the present invention is more objective and accurate. At the same time, the technology can be used for screening all embryos, and will be expected to greatly raise the accuracy of ART, reduce the risk of surgery. ease the pains of patients, and further improve the live birth rate of test-tube baby.

The beneficial effects brought by the present invention are shown as follows: 1. The method of the present invention performs further quantitative screening for a well-developed embryo based on traditional morphology and PGS. This method will increase the success rate of "test-tube baby" and reduce the abortion rate.

Compared with traditional embryonic morphology which relies on microscopy techniques to select embryos with a high morphological grade for transplantation, the method of the present invention is more objective and avoid the artificial uncertainty in morphological typing, since many morphological tests rely more on the personal experience of medical personnel. Moreover, the morphology quality can't represent the genomic and epigenomics status of a blastocyst, and cannot accurately predict the developmental state and potential of a blastocyst. However, the method of the present invention can directly measure and analyze the epigenetic information of embryos, accurately determine whether an embryo has a standard DNA methylation pattern and has the potential to develop into a healthy fetus, and at the same time determine whether chromosomes are normal, and thereby it may screen for an embryo which is well-developed and has normal chromosomes. The present PEGE method firstly proposes the concept of using epigenetic information to screen embryos and perform pre-transplantation testing.

2. The PEGE method of the present invention is superior to the PGS method currently in use.

PGD/PGS is a common used method in worldwide which can determine whether an embryo has chromosomal abnormality by analyzing DNA sequence and chromosomal structure. However, PGS/PGD method has no effect on most people without chromosomal abnormality and genetic disorder, and it is unable to improve the pregnancy rate and birth rate after ART in most people. By contrast, the non-invasive detection method for screening for a well-developed blastocyst of the present invention is applicable to all populations, and is also capable of detecting chromosomal abnormality. Therefore, the present PEGE method can not only determine the presence of chromosome aneuploidy which can be detected by current PGS method, but also can screen for embryos with better epigenetic status at the same time. Therefore, the present PEGE method has remarkable advantages over the current PGS method. Therefore, the present PEGE method has the potential to become the most common, most basic and most accurate clinical pre-transplantation screening method for embryos.

3. Prevention of Multi-Fetus Pregnancy and Reduction of Fetal Reduction Surgery.

Since the average success rate of 'test-tube baby' is about 20% to 30%. 2 or 3 blastocysts will be implanted into uterus at the same time in order to increase the success rate of one implantation. As a result, multi-fetus pregnancy often happens. Multi-fetus pregnancy is riskier than single pregnancy, and this risk exists for both mother and babies. Authoritative investigation shows that twins have a cesarean delivery rate of 78.45%. a premature birth rate of 47.07%, and a complication rate of 39.7%. Mothers of twins or multiple births have a higher risk of developing gestational syndromes such as diabetes and hypertension during pregnancy, and a higher probability of postpartum hemorrhage, and premature birth is also more likely to happen. Most premature babies are born with congenital lung diseases which will accompany them throughout their life. Hence, for the safety of mother and babies, fetal reduction needs to be carried out in principle when the number of fetus exceeds three. However, fetal reduction may also cause all embryos aborted at a possibility of 10%. The method of the present invention can avoid multi-fetus pregnancy resulting the implantation of several embryos in one implantation surgery, relieve the pain of mothers and improve the embryos survival rate and the rate of successful pregnancy.

BRIEF DESCRIPTION OF THE DRAWINGS

FIG. 5 is a functional analysis diagram of methylation reprogramming of different morphologically typed embryos. Functional enrichment analysis of differentially methylated regions between high grade and low grade embryos was performed. Genes with promoters located in DMRs were analyzed by DAVID GO enrichment analysis. The cis-regulatory elements of intergenic DMRs region were analyzed with GRE AT tools. GO analysis with P 0.05 had a statistical significance. The results indicate that regions having erroneous methylation often occur in basal metabolic genes that are important for cell survival or in genes involved in development, especially neurodevelopment, indicating that a normal methylation profile is critical for embryonic development.

SPECIFIC MODES FOR CARRYING OUT THE EMBODIMENTS

The following Examples further describe the present invention, but they are not intended to limit the range of the invention. The modifications and substitutions of the methods, procedures or conditions of the present invention made without departing from the spirit and essence of the present invention are intended to be included within the scope of the invention.

Unless particularly indicated, the chemical reagents used in the Examples are regular commercially available reagents. The technique means used in the Examples are those well known to a person skilled in the art.

Example 1: The Discovery of Instability of DNA Methylation on a Whole-Genome Level in Human Blastocyst In the present invention, blastocysts with different Gardner morphological grades including AA grade (highest grade) blastocysts and CC. BC and CB grade (low grade) blastocysts were collected. These blastocysts were from Peking University Third Hospital and the Third Affiliated Hospital of Guangzhou Medical University. When a patient accepted ART, several blastocysts were cultured in vitro, and then the blastocyst with the best morphology was transplanted into uterus. The patient then donated surplus blastocysts for scientific research on the subject of present invention after the informed consent form was signed by the patient. For each blastocyst, DNA methylation sequencing at single-base resolution was performed. "One-tube" experiments of the present invention were carried out as followed:
1. Sample preparation TE cells were biopsied from embryos, kept in 200 μl tubes with less than 5 μl of embryo culture medium or PBS buffer and then froze immediately at −80° C.

TABLE I

| Cell lysis buffer | | |
|---|---|---|
| Component | Volume | Final Concentration |
| Tris-EDTA (1M Tris, 0.1M EDTA) | 0.1 μl | 20 mM Tris, 2 mM EDTA |
| 1M KCl | 0.1 μl | 20 mM |
| 20 mg/ml QIAGEN proteaseK | 0.5 μl | 1 ug/μl |
| 10 mg/ml RNAse A | 0.5 μl | 1 ug/μl |
| Total Reaction Volume | 5 to 10 μl | |

The frozen sample was thawed quickly and centrifuged at 4° C. (3000 g, 5 min). Proteopepsis was performed at 56° C. for 1.5 h. Then the proteases were inactivated at 75° C. for 30 min. 3. DNA shearing Unmethylated Lambda DNA was added into the sample at a ratio of 5 pg Lambda DNA per 1000 pg DNA sample. The final sample volume was adjusted to 50 μl with ultra-pure water. Shearing conditions: S2, 50 μl, 400 bp. The volume of the sample was reduced to 30 μl by concentration.
4. End-Repair An End-repair buffer was prepared as follows:

| Component | Volume |
|---|---|
| T4 ligase buffer | 3.5 μl |
| NEBNext End Repair Enzyme Mix | 1.15 μl |
| dNTP mix (10 mM) | 0.35 μl |
| Digested Product | 30 μl |
| Total volume | 35 μl |

Reaction was performed for 30 min at 20° C., followed by enzyme inactivation at 75° C. for 20 min. Then the sample was subjected to a next step or was frozen at a temperature of −20° C. or lower.

5. dA-Tailing

The following regents were added into the product from step 4:

| Component | Volume |
| --- | --- |
| T4 ligase buffer | 0.5 μl |
| Klenow exo- | 1 μl |
| dATP (100 mM) | 0.4 μl |
| Digested product | 30 μl |
| Steriled ultra-pure water | 3 μl |
| Total volume | 40 μl |

Incubation was performed for 30 min at 37° C., followed by enzyme inactivation at 75° C. for 20 min. The sample was subjected to a next step, or was frozen at a temperature of −20° C. or lower.

6. Adapter Ligation

The following regents were added into the product from step 5:

| Component | Volume |
| --- | --- |
| T4 ligase buffer | 0.5 μl |
| Klenow exo- | 1 μl |
| dATP (100 mM) | 0.4 μl |
| Digested product | 30 μl |
| Steriled ultra-pure water | 3 μl |
| Total volume | 40 μl |

The mixture was mixed well, and incubated at 16° C. overnight (at least 8 h). Then the sample was subjected to a next step, or was frozen at a temperature of −20° C. or lower.

7. Methylation Library Preparation Kit

CT Conversion Reagent for 50 μl sample was formulated according to the instructions of the kit. A bisulfate conversion mixture was prepared as follows:

| Component | Volume |
| --- | --- |
| Adapter ligated mix | 50 μl |
| CT Conversion Reagent | 100 μl |
| Carrier RNA (1 μg/μl) | 0.5 μl |
| Total volume | 150 μl |

The mixture was mixed well, the sample was equally split into 2 tubes (75 μl sample per tube) and the running of the following program was performed: 98° C. for 10 min: 64° C. for 2 h; 4° C. for up to 2 h. A Spin Column was placed in a Collection tube and 600 μl binding buffer and 0.5 LI Carrier RNA were added to the column. 150 μl sample was added to the binding buffer. The mixture was mixed well by gentle and repeated pipetting, and then the cap was closed and placed for 5 min. Then the tube was centrifuged at 10,000 rpm or higher for 1 min. Reagents in the collection tube was added to the spin column and centrifugation of 1 min was performed again. The reagents after centrifugation were discarded. 100 μl Wash Buffer was added to the column, and centrifuged at 10,000 rpm or higher for 1 min. 200 μl De-sulphonation Buffer was added to the column, and the column was placed at room temperature for 15 to 20 min, then centrifuged at 10,000 rpm or higher for 1 min. The reagents after centrifugation were discarded. 100 μl Wash Buffer was added to the column again, and centrifuged at 10,000 rpm or higher for 1 min. The wash step was repeated, and the reagents in the collection tube were discarded, then the spin column was transferred to a new 1.5 ml centrifuge tube. 11 μl ultra-pure water was added, placed for 10 min at room temperature, and then centrifuged at 10,000 rpm or higher for 1 min, and this step was repeated again. The sample obtained after centrifugation was the Bisulfite treated DNA. The sample was subjected to a next step, or was frozen at a temperature of −20° C. or lower.

8. First Round of PCR Amplification

PCR Amplification kit was used, and the amplifying buffer was prepared as follows:

| Component | Volume |
| --- | --- |
| 2x PCR mix | 25 μl |
| 10 μM Primer 1.0 | 2.5 μl |
| 10 μM Index | 2.5 μl |
| Eluted DNA | 20 μl |
| Total volume | 50 μl |

Amplification was performed according to the following program: 98° C. for 45 s, 98° C. for 15 s, 65° C. for 30 s, 72° C. for 30 s (6 cycles in total): 72° C. for 1 min; and hold at 4° C.

The obtained sample was subjected to a next step, or frozen at a temperature of −20° C. or lower.

9. An equal volume (50 μl) of AMPure XP Beads was added to the DNA sample obtained from the above step, mixed well and centrifuged. Then the sample was placed at 37° C. for 10 min. The tube was placed on a magnetic rack for 5 min. The magnetic beads were washed with 200 μl of 75% ethanol and the supernatant was discarded. The magnetic beads were dried in air for 2 min to evaporate the ethanol. The magnetic beads were resuspended with 25 μl of 10 mM Tris-HCl (pH 8.5), centrifuged at a low speed, subject to standing for 5 min, and then placed on a magnetic rack for 5 min. The supernatant was collected into a new 200 μl centrifuge tube, and then subjected to a next step, or frozen at a temperature of −20° C. or lower.

10. Second Round of PCR Amplification

A PCR Amplification kit was used, and an amplifying buffer was prepared as follows:

| Component | Volume |
| --- | --- |
| 2x PCR mix | 25 μl |
| 10 μM Primer 1.0 | 2.5 μl |
| 10 μM Index | 2.5 μl |
| Eluted DNA | 20 μl |
| Total volume | 50 μl |

Amplification was performed according to the following program: 98° C. for 45 s, 98° C. for 15 s, 65° C. for 30 s, 72° C. for 30 s (13 to 16 cycles in total); 72° C. for 1 min; and hold at 4° C. The obtained sample was subjected to a next step, or frozen at a temperature of −20° C. or lower.

11. Gel extraction

DNA sample was subjected to agarose gel electrophoresis with an agarose concentration of 2% and a voltage of 90V. DNA fragments with an appropriate size were cut out for gel extraction according to the requirement of sequencing. For the last step of gel extraction, DNA was eluted for three times with a total volume of 50 μl sterile ultra-pure water.

12. Removal of Adapter 0.8× AMPure XP Beads (40 μl) was added to the DNA sample obtained from the above step, mixed well, and centrifuged. The mixture was stood at 37° C. for 10 min. The tube was placed on the magnetic rack for 5 min for absorption of beads. The supernatant was carefully discarded without touching the beads. The beads were washed with 200 μl 75% ethanol, and then the supernatant was discarded. The beads were dried in air for 2 mm to evaporate ethanol. The beads were resuspended with 15 μl of 10 mM Tris-HCl (pH 8.5), centrifuged at a low speed, subjected to standing for 5 min, and then placed on a magnet rack for 5 min. Supernatant was collected into a new 1.5 mL centrifuge tube and stored at −20° C., The obtained sample was the DNA sample to be sequenced.

A DNA methylation library was obtained through above procedures. and the library can be sequenced after passing library quality inspection. The obtained blastocyst whole-genome methylation sequencing data was first mapped to a human reference sequence (hg19) by Bismark alignment software. According to mapping information, the unique read mapped to the human reference sequence was divided into Watson and Crick chain fragments after the PCR repeat fragment and the double-ended fragment overlap region were removed. The methylation status of cytosine on the Waston chain fragment and adenine on the Crick chain fragment were obtained with Samtools software, respectively. Then the information about the two chains was combined to obtain the DNA methylation level at each CpG site. The whole-genome methylation level was the average value of DNA methylation levels at all CpG sites.

Figure 2:
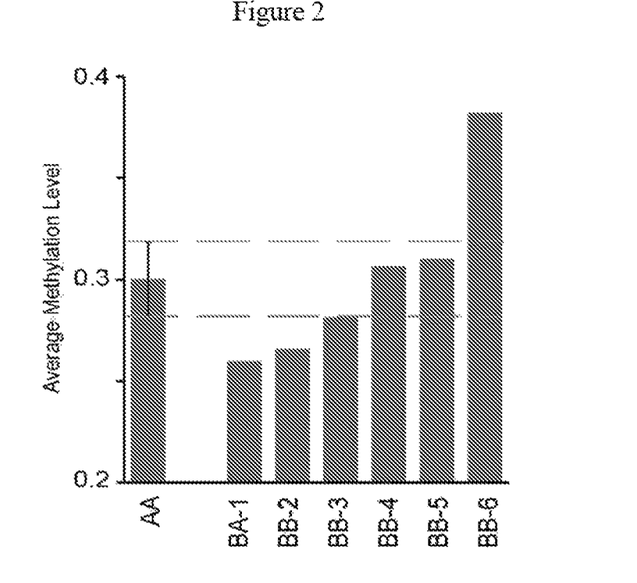
FIG. 2 is a graph showing the DNA methylation levels of 6 (BB/BA) embryos. Two dashed lines indicate the SD of the DNA methylation level for five AA grade embryos. The results show that the DNA methylation levels of three embryos (BB-3, BB-4, and BB-5) are similar with AA grade embryos, while the DNA methylation levels of remaining three embryos (BA-1, BB-2, and BB-6) are very different from that of AA grade embryos.

Analysis showed that the DNA methylation levels of 5 AA grade blastocysts were similar. However, the DNA methylation levels of 6 out of 7 low grade embryos were significantly deviated from the average DNA methylation level of AA grade embryos, and the difference between low grade embryos was also obvious. Compared to the high grade embryos, those low grade embryos were either over de-methylated or not sufficiently de-methylated (FIG. 1). For BA or BB grade embryos, 3 out of 6 embryos were good candidates for embryo transplantation because their DNA methylation levels were similar to that of AA grade embryos, whereas the rest were not suitable for embryo transplantation (FIG. 2).

Further, the principal component analysis (PCA) for bioinformatical DNA methylation pattern showed that the DNA methylation pattern of all 5 AA embryos were very similar and can be clustered together (indicated by the circle in FIG. 3). In contrast, 7 low grade embryos distributed outside of the circle, and the DNA methylation pattern of these embryos were quite different from that of AA grade embryos.

An analysis comparing DNA methylation status of the same functional elements regions of different embryos showed that the DNA methylation patterns of 5 AA grade embryos were similar for the same functional element region. However, in low grade embryos, the methylation status of the same functional element region differs from each other (FIG. 4). It can be seen that, epigenetic instability on whole-genome level frequently occurs during human early embryonic development, and the DNA methylation levels of AA embryos are quite similar (i.e., different embryos show the same high or low methylated status in the same genomic regions). The low grade embryos in morphologic classification (including B* and C*), show different levels of divergence in DNA methylation status. The lower the morphological grade, the greater the deviation from the DNA methylation level of AA embryos. Since the birth rate of AA grade embryos are the highest and the DNA methylation levels of AA embryos are quite similar, it is considered that the DNA methylation pattern of AA grade embryos is the most correct and can be used to guide normal early embryogenesis.

Example 2. Abnormal Methylation Reprogramming Affected Signaling Pathways Regulating Early Embryonic Development Analysis of gene function of regions showing different methylation status in high grade embryos and low grade embryos was performed (gene ontology).

The analysis found that the genes with promoters located in differentially methylated regions (DMRs) were enriched in many pathways related to embryonic development, including cell cycle, DNA metabolism, DNA modification, chromosome localization, RNA processing, DNA repair and the like (FIG. 5). Genes with intergenic DMRs were mainly involved in development of specific tissues, such as neuron development, neuronal differentiation and cell fate determination, structure of spinal cord, and steady state of mRNA (FIG. 5).

The results also showed that methylations in enhancers were often falsely reprogramed in CC grade (lowest grade) embryos. The genes with DMRs located within enhancers were enriched in development and metabolism related pathways. FIG. 6 shows the methylation status of IDH2 gene's enhancer and flanked regions in different embryos. AA grade embryos showed a hypomethylation status in this region, while CC grade embryos showed a hypermethylation status in this region. Hypermethylation of the enhancer region caused a significant decrease in the expression of the IDH2 gene.

Example 3. Relationship Between the DNA Methylation Level of Blastocysts Before Implantation and the Birth Rate after ART In this Example, the average DNA methylation level of AA grade blastocysts was 0.3±0.02 was used as a standard, i.e., a quantitative standard for non-invasive detection of blastocysts before clinical implantation. This standard, which is based on morphological examination, is a brand new clinical indicator for accurately screening for well-developed blastocysts. To further validate the accuracy of this indicator, six B* grade blastocysts were collected for analysis (FIG. 2). The results show that three of them had a DNA methylation level which was significantly divergent from the standard which was the average DNA methylation level of AA grade blastocysts of 0.3. FIG. 1 shows that the DNA methylation level of one out of five AA grade embryos was divergent from the standard, while six out of seven C* embryos diverged from the standard. The rate of blastocysts meeting the standard in AA, B*, and C* grade embryos were 80%, 50%, and 14%, respectively (FIG. 7). The results of FIG. 7 show that the proportion of blastocysts with a DNA methylation level meeting the standard in embryos at different grades was positively correlated with the clinical birth rate of embryos at corresponding grade.

The results of the present Example demonstrate that genomic DNA methylation profile is critical during embryonic development, and blastocysts with a DNA methylation level close or equal to the standard are ideal candidates for embryo transplantation.

Example 4. Pre-Implantation Epigenetic Examination Achieved by a Few of TE Cells Biopsied from Blastocyst Through Micromanipulation Techniques Clinically, pre-implantation genetic diagnosis (PGD) technology has been used for more than 20 years, which use biopsy to remove a few of cells from blastocysts for the diagnosis of diseases such as genetic mutations and chromosomal abnormalities. In the present Example, a few of cells were biopsied from trophectoderm cells of each blastocyst to be tested, and the TE cell methylation library of 5 different blastocysts was constructed using the "One Tube" trace-cell whole-genome methylation library method as described in Example 1 respectively, while the remaining cells of the different blastocysts were used for constructing parallel methylation libraries. Then whole-genome methylation sequencing was performed using the Hiseq sequencing platform. FIG. 8 shows that the DNA methylation level of a few of non-invasively biopsied TE cells was similar to the DNA methylation level of the whole embryo, so the methylation profile of TE cells can represent the methylation profile of a whole embryo. Therefore, this non-invasive detection method through biopsy can be used to screen for blastocysts with better DNA methylation profile before embryo transplantation.

Example 5: Detection of Chromosome Aneuploidy of Embryos

Figure 9:
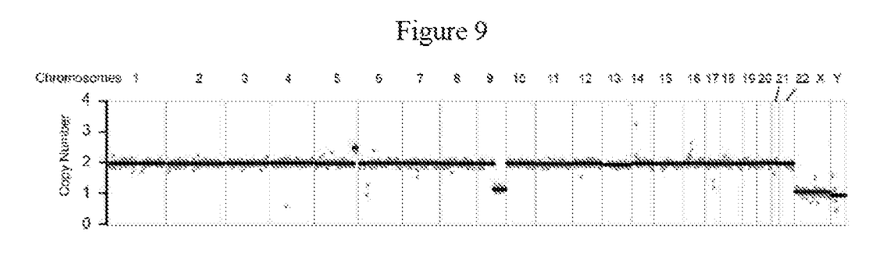
FIG. 9 is a graph showing analysis of the chromosomal copy number based on the result of DNA methylation profile. One extra copy of one fragment of chromosome 5 and lack of one copy of one fragment of chromosome 9 are found in sample s-25, indicating that the chromosome of the embryo is abnormal, and this embryo is not suitable for embryo transplantation.

At present, PGD/PGS is a commonly used method in worldwide which can determine whether embryos have chromosomal abnormality by analyzing DNA sequence and chromosomal structure of embryos. The whole-genome DNA methylation sequencing results of the present invention can also be used to evaluate chromosomal ploidy and the algorithm for chromosomal abnormality performs examination based on the sequencing depth of the chromosomal fragments. For whole-genome methylation sequencing data of blastocyst after alignment, the sequencing depth was calculated in units of 1 Mb, after removing factors such as GC content and the alignment preference. Chromosomes were then segmented according to similarity between the sequencing depth by hidden Markov chain model (HMM). Extremely high or low sequencing depth of a region indicates chromosome doubling or deletion in this segment. The results of Table 2 demonstrate that 17 out of 36 embryos had chromosomal abnormality, and those embryos were not suitable for implantation. Taking sample s-25 for example, one extra copy of one fragment of chromosome 5 and lack of one copy of one fragment of chromosome 9 were found (FIG. 9).

Therefore, The PEGE method of the present invention can not only determine the presence of chromosomal aneuploidy which also can be done by PGS, but also screen embryos with better epigenetic status at the same time, and thus the method is obviously better than the existing PGS method. Therefore, the PEGE method may be expected to be a most conventional, basic and accurate pre-implantation screening method for embryos. The PEGE method of the present invention can detect chromosomes abnormalities at the same time, and it is found that the chromosomes of 17 embryos have chromosomal abnormalities, and these embryos cannot be used for embryo transplantation at all.

TABLE 2

Detection of chromosome ploidy of 17 embryos by the method of the present invention

| Sample No. | Allosome XX/XY | Chromosomal abnormality |
|---|---|---|
| 1_4AA_350 | XY | |
| 11_3CC_sort | XY | |
| 13_6AA_sort | XY | |
| 2-4CC_sort | XX | |
| 7_3CC_sort | XX | |
| 8-3CC-350 | XY | |
| 9-3CC-350 | X | \+7 |
| BL-1-2CB | XY | |
| BL-1-4AA | XX | |
| BL-2-2CC | XY | −21 |
| BL-2-4AA | XY | −19 |
| MLCC-19 | XX | \+8, −18 |
| MLCC-20 | XX | |
| MLCC-21 | XY | \+4 |
| s_11-4BA | XX | −22 |
| s_12-4CB | XY | |
| s_13-5CB | XY | \−15, +17 |
| s_15-4CA | XY | −20 |
| s_16-4BA | XX | \+22, +2 |
| s_17-4CC | XY | \+2, +8, −16, −18, +21 |
| s_25-4CC | XY | \+5Q, −9Q |
| s_31-5BC | XY | \−21, −22 |
| s_32-5CC | XX | \+22 |
| s_43-4BB | XY | |
| s_44-4CC | XY | |
| s_54-4BC | XX | −14 |
| s_6-4BB | XX | \+1P |
| s_6-5AA | XY | \−1P, −4P |
| s1 | XX | |
| s4AA-13 | XY | |
| s4AA-14 | XY | |
| s4CC-22 | XY | |
| s4CC-23 | XX | |
| s4CC-24 | XY | |
| s4CC-25 | XX | |
| s4CC-26 | X | −X |

Although the invention is described in detail in the general description and specific embodiments hereinbefore, it is obvious to a person skilled in the art that some modifications or improvements can be made based on the present invention. Therefore, all these modifications or improvements made on the basis of the present invention without departing from the spirit of the present invention fall into the protection scope claimed in the present invention.

INDUSTRIAL APPLICABILITY

The present invention provides a non-invasive detection method for screening for a well-developed blastocyst. A DNA methylation profile of a few of trophectoderm cells in blastocyst is detected, the average DNA methylation level and the DNA methylation pattern of embryos with a good morphology in Gardner morphological blastocyst grading process are used as the standard for screening for a well-developed blastocyst, and the nearer the DNA methylation level of the trophectoderm cells of the blastocyst to be tested approaches the DNA methylation level or state of good embryos, the better the embryo development is and the higher the suitability for being implanted into a maternal subject is. Furthermore, results of methylation sequencing may be analyzed to determine whether a chromosome is abnormal, so as to directly remove chromosome-abnormal embryos. The non-invasive detection method for screening for a well-developed blastocyst provided by the present invention can help clinicians select blastocysts with normal chromosomal ploidy and better epigenetic status for embryo transplantation, and can greatly improve the accuracy of ART, reduce spontaneous abortion rate, improve the quality of pregnancy and increase the birth rate of "test tube baby". The method has a high economic value and a good application prospect.

What is claimed is:

1. A method of selecting, and then implanting, a selected human blastocyst into a human subject which comprises:
   (a) obtaining samples of biopsied human trophectoderm cells from each of multiple human blastocysts from a single donor;
   (b) constructing a DNA methylome library from, and sequencing the DNA methylome of, each of the samples of biopsied trophectoderm cells,
   (c) calculating the global DNA methylation level for each of the samples of the biopsied trophectoderm cells based on the sequences of the DNA methylome obtained in step (b) by counting (i) the number of methylated CpGs and (ii) the number of all CpGs and determining the ratio of (i) to (ii) for each of the samples and thereby the global methylation level of each of the blastocysts from which each sample of trophectoderm cells was obtained;
   (d) selecting the human blastocyst for use in implantation which has the global DNA methylation level which is closest to 0.30; and
   (e) implanting the human blastocyst selected in step (d) into the human subject.

* * * * *